US012626786B2

(12) United States Patent
Gu et al.

(10) Patent No.: US 12,626,786 B2
(45) Date of Patent: May 12, 2026

(54) METHOD AND SYSTEM FOR PREDICTING WORKING CONDITIONS OF LITHIUM BATTERIES

(71) Applicant: Makesense Energy Technology Co., Limited, Shanghai (CN)

(72) Inventors: Danfei Gu, Shanghai (CN); Mingchen Jiang, Shanghai (CN); Siyuan Chen, Shanghai (CN); Weikun Wu, Shanghai (CN); Pei Song, Shanghai (CN); Enhai Zhao, Shanghai (CN); Xiao Yan, Shanghai (CN); Xiaohua Chen, Shanghai (CN); Peng Ding, Shanghai (CN); Pingchao Hao, Shanghai (CN)

(73) Assignee: Makesense Energy Technology Co., Limited., Shanghai (CN)

( * ) Notice: Subject to any disclaimer, the term of this patent is extended or adjusted under 35 U.S.C. 154(b) by 319 days.

(21) Appl. No.: 18/206,683

(22) Filed: Jun. 7, 2023

(65) Prior Publication Data

US 2023/0410949 A1     Dec. 21, 2023

(30) Foreign Application Priority Data

Jun. 17, 2022     (CN) .......................... 202210689858.8

(51) Int. Cl.
*G16C 20/10* (2019.01)
*G01D 21/02* (2006.01)
(Continued)

(52) U.S. Cl.
CPC ............. *G16C 20/10* (2019.02); *G01D 21/02* (2013.01); *G01R 31/367* (2019.01); *G16C 10/00* (2019.02); *G16C 20/30* (2019.02)

(58) Field of Classification Search
None
See application file for complete search history.

(56) References Cited

U.S. PATENT DOCUMENTS

| | | | | |
|---|---|---|---|---|
| 6,502,046 B1 * | 12/2002 | Yoon | .................. | G01R 31/2839 |
| | | | | 324/76.23 |
| 10,298,026 B2 * | 5/2019 | Trimboli | ........... | H02M 3/33507 |

(Continued)

FOREIGN PATENT DOCUMENTS

| | | | | |
|---|---|---|---|---|
| CN | 108710767 A | * 10/2018 | ............. | G06F 30/20 |
| CN | 111027174 A | * 4/2020 | ............. | G06F 17/14 |

(Continued)

*Primary Examiner* — Kevin R Steckbauer
(74) *Attorney, Agent, or Firm* — troutman pepper locke; Tim Tingkang Xia, Esq.

(57) ABSTRACT

The invention discloses method and system for predicting working conditions of lithium batteries. The method includes performing a Fourier transform on a physicochemical state quantity distribution function of a solid-phase lithium battery to calculate a physicochemical state quantity distribution series function in a frequency domain and obtain a solid-phase physicochemical state quantity in the frequency domain according to the physicochemical state quantity distribution series function; performing a Laplace transform on a partial differential governing equation set of the solid-phase physicochemical state quantity to obtain a solid-phase ordinary differential equation set in a complex frequency domain and obtain an analytical solution in the time domain through an inverse Laplace transform; and calculating, according to the analytical solution, a predicted value of the working conditions of the solid-phase lithium battery at any location and at any time in the future.

10 Claims, 2 Drawing Sheets

(51) Int. Cl.
   *G01R 31/367* (2019.01)
   *G16C 10/00* (2019.01)
   *G16C 20/30* (2019.01)

(56) References Cited

U.S. PATENT DOCUMENTS

| | | | | | |
|---|---|---|---|---|---|
| 10,985,572 | B2 * | 4/2021 | Duan | ...................... | H02J 3/46 |
| 11,847,383 | B2 * | 12/2023 | Lu | ........................... | G06F 30/13 |
| 12,377,747 | B2 * | 8/2025 | Andersson | ............. | B60L 53/62 |
| 2016/0336765 | A1 * | 11/2016 | Trimboli | ............... | H02J 7/0068 |
| 2020/0106273 | A1 * | 4/2020 | Duan | ..................... | G06N 3/048 |
| 2021/0049245 | A1 * | 2/2021 | Baehr-Jones | .......... | G06F 17/13 |
| 2021/0091866 | A1 * | 3/2021 | Zhang | ................. | H04B 17/309 |
| 2022/0032805 | A1 * | 2/2022 | Andersson | ............. | B60L 53/65 |
| 2022/0207211 | A1 * | 6/2022 | Baehr-Jones | .......... | G06F 17/13 |
| 2023/0195953 | A1 * | 6/2023 | Lu | ........................... | G06F 17/14 |
| | | | | | 703/1 |
| 2023/0410949 | A1 * | 12/2023 | Gu | ......................... | G01D 21/02 |
| 2024/0046011 | A1 * | 2/2024 | Baehr-Jones | .......... | G06F 30/20 |
| 2024/0175927 | A1 * | 5/2024 | Jiang | ..................... | G01R 31/36 |
| 2025/0123331 | A1 * | 4/2025 | Zhang | ................... | H01M 10/42 |
| 2025/0244732 | A1 * | 7/2025 | Casasnovas Gonzáles | ................. | |
| | | | | | H02J 7/007 |

FOREIGN PATENT DOCUMENTS

| | | | | | |
|---|---|---|---|---|---|
| CN | 111239610 | A | * | 6/2020 | ........... G01R 31/374 |
| CN | 111444625 | A | * | 7/2020 | ............. G06F 17/13 |
| CN | 111239610 | B | * | 5/2021 | ........... G01R 31/367 |
| CN | 113933713 | A | * | 1/2022 | ......... G01R 31/3648 |
| CN | 115062474 | A | * | 9/2022 | ............. G06F 17/14 |
| CN | 115064222 | A | * | 9/2022 | ............. G16C 20/20 |
| CN | 115081207 | A | * | 9/2022 | ............. G06F 17/13 |
| CN | 115241551 | A | * | 10/2022 | ........... H01M 10/42 |
| CN | 115062474 | B | * | 1/2023 | ............. G06F 30/20 |
| CN | 115081207 | B | * | 3/2023 | ............. G06F 17/13 |
| CN | 115935635 | A | * | 4/2023 | ............. G01R 31/36 |
| CN | 116504322 | A | * | 7/2023 | ............. G16C 10/00 |
| CN | 117035095 | A | * | 11/2023 | ............. G06N 5/041 |
| CN | 111444625 | B | * | 1/2024 | ............. G06F 17/13 |
| CN | 117390348 | A | * | 1/2024 | ............. G06F 17/13 |
| CN | 115935635 | B | * | 2/2024 | ............. G01R 31/36 |
| CN | 117390348 | B | * | 4/2024 | ............. G06F 17/13 |
| CN | 117686919 | B | * | 4/2024 | ............. G06F 17/11 |
| CN | 117849642 | A | * | 4/2024 | ........... G01R 31/367 |
| CN | 118104038 | A | * | 5/2024 | ............. G05B 17/02 |
| CN | 115064222 | B | * | 7/2024 | ............. G01D 21/02 |
| CN | 118734574 | A | * | 10/2024 | ............. G06F 17/13 |
| CN | 120294582 | A | * | 7/2025 | ........... G01R 31/378 |
| EP | 3869223 | A1 | * | 8/2021 | ............. B60L 50/20 |
| EP | 3736587 | B1 | * | 11/2023 | ............. G01R 31/382 |
| JP | 2024534226 | A | * | 9/2024 | ........ G01R 31/3648 |
| KR | 20180082936 | A | * | 7/2018 | ........ G01R 31/3651 |
| KR | 20220007028 | A | * | 1/2022 | ............. G06F 17/17 |
| KR | 20220007029 | A | * | 1/2022 | ............. B60L 58/16 |
| WO | WO-2022031059 | A1 | * | 2/2022 | ........... G01R 31/396 |
| WO | WO-2023066469 | A1 | * | 4/2023 | ........... G05B 17/02 |

* cited by examiner

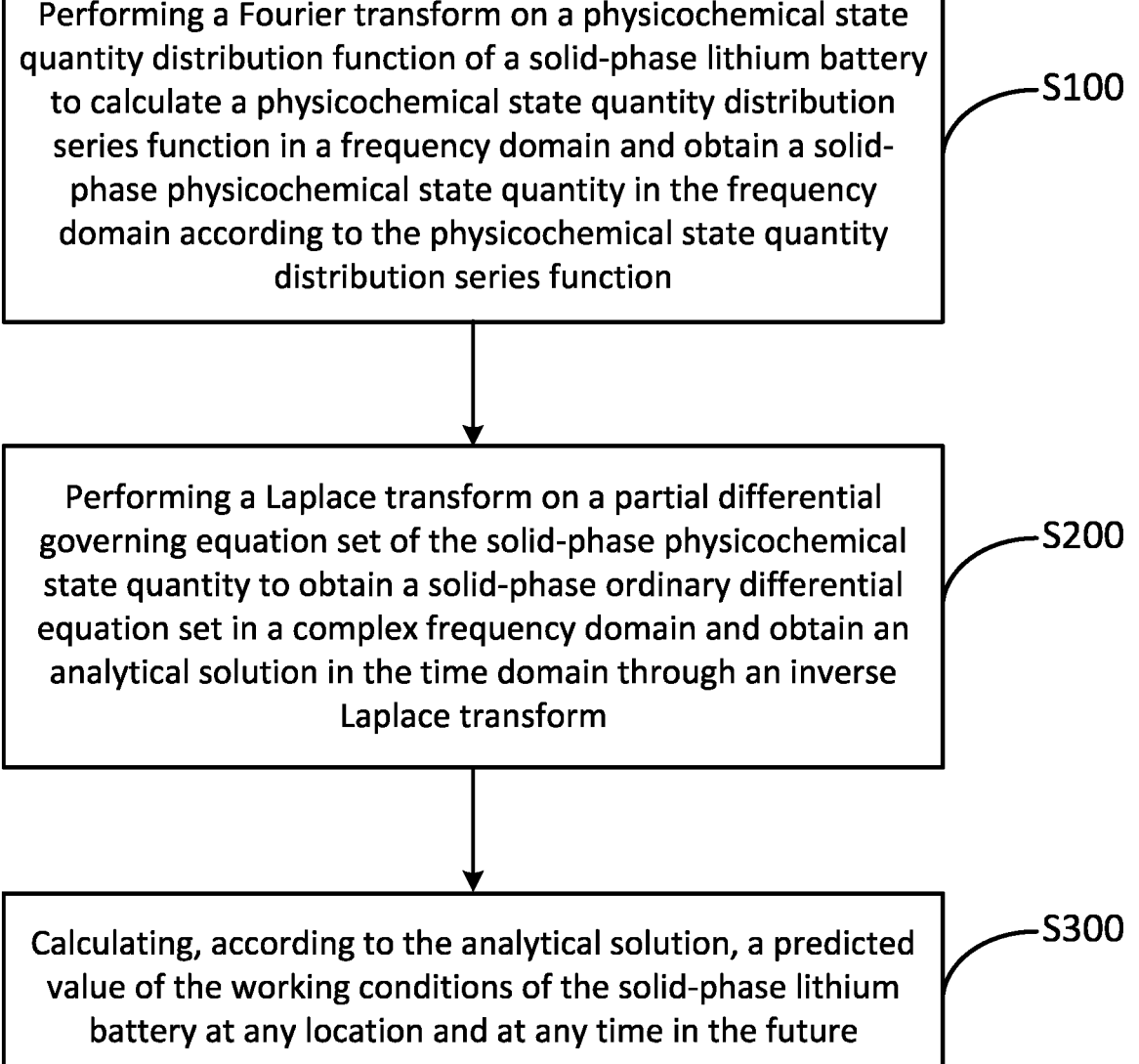

Performing a Fourier transform on a physicochemical state quantity distribution function of a solid-phase lithium battery to calculate a physicochemical state quantity distribution series function in a frequency domain and obtain a solid-phase physicochemical state quantity in the frequency domain according to the physicochemical state quantity distribution series function ⸺S100

Performing a Laplace transform on a partial differential governing equation set of the solid-phase physicochemical state quantity to obtain a solid-phase ordinary differential equation set in a complex frequency domain and obtain an analytical solution in the time domain through an inverse Laplace transform ⸺S200

Calculating, according to the analytical solution, a predicted value of the working conditions of the solid-phase lithium battery at any location and at any time in the future ⸺S300

FIG. 1

METHOD AND SYSTEM FOR PREDICTING WORKING CONDITIONS OF LITHIUM BATTERIES

CROSS-REFERENCE TO RELATED PATENT APPLICATION

This application claims priority to and the benefit of Chinese Patent Application No. 202210689858.8 filed Jun. 17, 2022, which are incorporated herein in their entireties by reference.

FIELD OF THE INVENTION

The invention relates generally to the field of batteries, and more particularly to method and system for predicting working conditions of lithium batteries.

BACKGROUND OF THE INVENTION

In the context of global "carbon neutral", the search for clean energy that can replace petroleum energy continues to heat up. Solar energy, tidal energy, wind energy, water energy, etc. are clean and sustainable energy sources, but the controllability of media that generate energy is relatively not very strong. Lithium batteries are currently a new generation of batteries, which have high energy density and long cycle life, and are widely used in mobile communications, digital technology, electric vehicles, energy storage and other fields. The demand for lithium batteries and materials thereof in the future is incalculable, and the corresponding upstream and downstream industrial chains have a huge market, which makes the research on lithium battery simulation a research hotspot.

The current mainstream electrochemical model simulation methods use finite difference methods, finite element methods, finite volume methods, fitting function methods, and methods to simplify physical and chemical control conditions to simulate electrochemical models. Using discrete iterative solutions such as the finite difference methods, the finite element methods, and the finite volume methods requires high computational power on the computation end, and the calculation is slow, which make it impossible to perform electrochemical calculations of high-flux multi-batteries. However, the solution method using the fitting function methods and the methods of simplifying the physical and chemical control conditions is only an approximate solution and a simplified solution of the governing equation, and the accuracy of the solution is not high, which may bring cumulative errors to the actual applications.

In the current battery early warning algorithms, the early warning of the battery is mostly based on threshold judgment of macroscopic quantity, or based on a black box obtained by machine learning of macroscopic quantity change and possibly occurring events through big data. However, in the actual lithium battery, each macroscopic physical quantity inside the lithium battery has a great relationship with whether the lithium battery can continuously and efficiently operate safely and healthily. Therefore, how to accurately predict the working condition of the lithium battery is a technical problem that needs to be solved urgently.

SUMMARY OF THE INVENTION

In view of the above-noted shortcomings of the prior art, one of the objectives of this invention is to provide lithium battery working condition prediction method and system to solve the technical problems that the future working condition of the lithium battery cannot be accurately predicted in the prior art, and further the thermal safety problem of the lithium battery under different working conditions cannot be prevented in time.

In one aspect of the invention, the method comprises performing a Fourier transform on a physicochemical state quantity distribution function of a solid-phase lithium battery to calculate a physicochemical state quantity distribution series function in a frequency domain and obtain a solid-phase physicochemical state quantity in the frequency domain according to the physicochemical state quantity distribution series function, wherein the physicochemical state quantity distribution function is an equation expression of physical and chemical quantities of the solid-phase lithium battery that change continuously in space in a time domain, and wherein the physical and chemical quantities comprise at least one state quantity of physical parameters and chemical parameters of the solid-phase lithium battery; performing a Laplace transform on a partial differential governing equation set of the solid-phase physicochemical state quantity to obtain a solid-phase ordinary differential equation set in a complex frequency domain and obtain an analytical solution in the time domain through an inverse Laplace transform; and calculating, according to the analytical solution, a predicted value of the working conditions of the solid-phase lithium battery at any location and at any time in the future.

In one embodiment, said performing the Fourier transform on the physicochemical state quantity distribution function of the solid-phase lithium battery comprises performing a cosine Fourier transform on the physicochemical state quantity distribution function of the solid-phase lithium battery before relaxation; and calculating the physicochemical state quantity distribution series function in the frequency domain.

In one embodiment, the partial differential governing equation set of the solid-phase physical chemical quantity comprises a governing equation, a boundary condition and an initial condition, wherein the governing equation is a mathematical expression that characterizes an electrochemical model of the solid-phase lithium battery for a spatial distribution of the physical and chemical quantities as a function of time, the boundary condition is an exchange condition of a solid phase and the outside, and the initial condition is an initial value of the physicochemical state quantity distribution function.

In one embodiment, said performing the Laplace transform on the partial differential governing equation set of the solid-phase physicochemical state quantity comprises performing a frequency domain conversion on the governing equation and the boundary condition based on the Laplace transform to obtain a complex frequency domain governing equation and a complex frequency domain boundary condition, so as to obtain a solid-phase ordinary differential equation set in the complex frequency domain, wherein the complex frequency domain solid-phase ordinary differential equation set comprises the complex frequency domain governing equation, the complex frequency domain boundary condition and the physicochemical state quantity distribution series function in the frequency domain; and solving the complex frequency domain solid-phase ordinary differential equation set, and calculating the solved result using the inverse Laplace transform to obtain the analytical solution of infinite series in the time domain.

3                                                                                        4

In one embodiment, said calculating the predicted value of the working conditions of the solid-phase lithium battery comprises substituting spatial coordinates and future time of a state quantity to be solved into the corresponding analytical solution to calculate the predicted values of the working conditions of the solid-phase lithium battery at the future time and the location corresponding to the spatial coordinates.

In one embodiment, said calculating the predicted value of the working conditions of the solid-phase lithium battery comprises comparing the predicted value of the working conditions with a corresponding threshold value; and generating prompt information for notification and early warning, when the predicted value of the working conditions exceeds the corresponding threshold value.

In another aspect of the invention, the system for predicting working conditions of lithium batteries comprises a first calculation module, configured to perform a Fourier transform on a physicochemical state quantity distribution function of a solid-phase lithium battery to calculate a physicochemical state quantity distribution series function in a frequency domain and obtain a solid-phase physicochemical state quantity in the frequency domain according to the physicochemical state quantity distribution series function, wherein the physicochemical state quantity distribution function is an equation expression of physical and chemical quantities of the solid-phase lithium battery that change continuously in space in a time domain, and wherein the physical and chemical quantities comprise at least one state quantity of physical parameters and chemical parameters of the solid-phase lithium battery.

The system further comprises a second calculation module, configured to perform a Laplace transform on a partial differential governing equation set of the solid-phase physicochemical state quantity to obtain a solid-phase ordinary differential equation set in a complex frequency domain and obtain an analytical solution in the time domain through an inverse Laplace transform; and a prediction module, configured to calculate a predicted value of the working conditions of the solid-phase lithium battery at any location and at any time in the future according to the analytical solution.

In one embodiment, the first calculating module comprises a first conversion unit, configured to perform a cosine Fourier transform on the physicochemical state quantity distribution function of the solid-phase lithium battery before relaxation; and calculate the physicochemical state quantity distribution series function in the frequency domain.

In one embodiment, the partial differential governing equation set of the solid-phase physical chemical quantity comprises a governing equation, a boundary condition and an initial condition, wherein the governing equation is a mathematical expression that characterizes an electrochemical model of the solid-phase lithium battery for a spatial distribution of the physical and chemical quantities as a function of time, the boundary condition is an exchange condition of a solid phase and the outside, and the initial condition is an initial value of the physicochemical state quantity distribution function.

In one embodiment, the second calculation module comprises a second conversion unit, configured to perform a frequency domain conversion on the governing equation and the boundary condition based on the Laplace transform to obtain a complex frequency domain governing equation and a complex frequency domain boundary condition, so as to obtain a solid-phase ordinary differential equation set in the complex frequency domain, wherein the complex frequency domain solid-phase ordinary differential equation set comprises the complex frequency domain governing equation, the complex frequency domain boundary condition and the physicochemical state quantity distribution series function in the frequency domain; and an inverse Laplace calculation unit, configured to solve the complex frequency domain solid-phase ordinary differential equation set, and calculate the solved result using the inverse Laplace transform to obtain the analytical solution of infinite series in the time domain.

In one embodiment, the prediction module comprises a prediction unit, configured to substitute spatial coordinates and future time of a state quantity to be solved into the corresponding analytical solution to calculate the predicted values of the working conditions of the solid-phase lithium battery at the future time and the location corresponding to the spatial coordinates.

In one embodiment, the system further comprises a comparison module, configured to compare the predicted value of the working conditions with a corresponding threshold value; and an alarm module, configured to generate prompt information for notification and early warning, when the predicted value of the working conditions exceeds the corresponding threshold value.

Compared with the prior art, the method and the system for predicting the working conditions of the lithium batteries of the invention have the advantages that the predicted values of the working conditions of the lithium battery at different times and different locations are obtained by solving and calculating through the Fourier transform and the Laplace transform, the working condition prediction accuracy of the lithium batteries can be greatly improved, and the computation cost is reduced.

BRIEF DESCRIPTION OF THE DRAWINGS

The accompanying drawings illustrate one or more embodiments of the invention and, together with the written description, serve to explain the principles of the invention. The same reference numbers may be used throughout the drawings to refer to the same or like elements in the embodiments.

FIG. 1 is a flow chart of a method for predicting operating conditions of lithium batteries according to one embodiment of the invention.

DETAILED DESCRIPTION OF THE INVENTION

Figure 2:
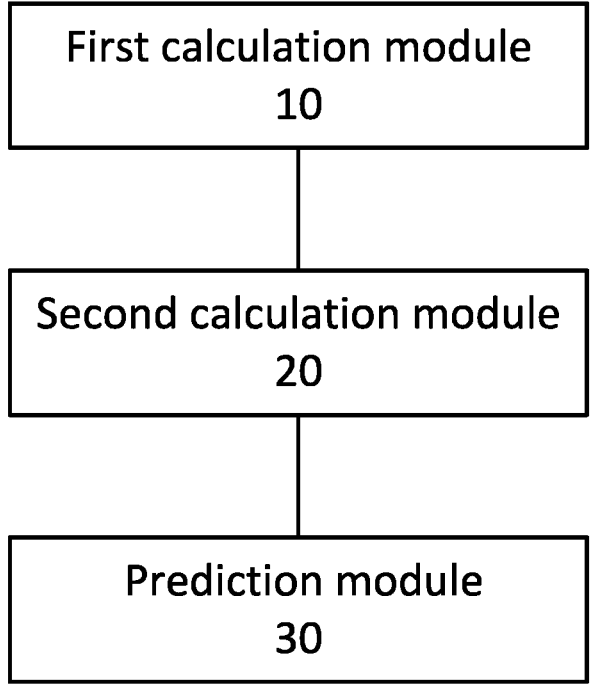
FIG. 2 is a schematic block diagram of a system for predicting operating conditions of lithium batteries according to one embodiment of the invention.

In the following description, for purposes of explanation and not limitation, specific details are set forth, such as particular system structures, techniques, etc. in order to provide a thorough understanding of the embodiments of the invention. It will be apparent, however, to one skilled in the art that the invention may be practiced in other embodiments that depart from these specific details. In other instances, detailed descriptions of well-known systems, devices, circuits, and methods are omitted so as not to obscure the description of the invention with unnecessary details.

It will be understood that the terms "comprises" and/or "comprising," when used in this specification and the appended claims, specify the presence of stated features, integers, steps, operations, elements, and/or components, but do not preclude the presence or addition of one or more other features, integers, steps, operations, elements, components, and/or groups thereof.

For the sake of simplicity, the drawings only schematically show the parts relevant to the invention, and they do not represent the actual structure as a product. In addition, in order to make the drawings concise and understandable, components having the same structure or function in some of the drawings are only schematically illustrated or only labeled. In the disclosure, "one" means not only "only one" but also a case of "more than one".

It should be further understood that the term "and/or" as used in the disclosure and the appended claims refers to and includes any and all possible combinations of one or more of the associated listed items.

In addition, in the description of the invention, the terms "first", "second", and the like are used only for distinguishing the description, and are not intended to indicate or imply relative importance.

In order to more clearly illustrate the embodiments of the invention or the technical solutions in the prior art, the following description will be made with reference to the accompanying drawings of FIGS. 1-2. It is obvious that the drawings in the following description are only some examples of the invention, and that for a person skilled in the art, other drawings and embodiments can be derived from them without inventive effort.

Referring to FIG. 1, a schematic flowchart of a method for predicting a working condition of a lithium battery is shown according to one embodiment of the invention. In the exemplary embodiment, the method includes the following steps.

At step S100, performing a Fourier transform on a physicochemical state quantity distribution function of a solid-phase lithium battery to calculate a physicochemical state quantity distribution series function in a frequency domain and obtain a solid-phase physicochemical state quantity in the frequency domain according to the physicochemical state quantity distribution series function, wherein the physicochemical state quantity distribution function is an equation expression of physical and chemical quantities of the solid-phase lithium battery that change continuously in space in a time domain, and wherein the physical and chemical quantities comprise at least one state quantity of physical parameters and chemical parameters of the solid-phase lithium battery.

Specifically, the physical and chemical quantities are used to characterize macroscopic physical and chemical parameters of the lithium battery and can indicate the working condition of the lithium battery, and the physical parameters of the solid-phase lithium battery comprise a solid-phase voltage, a solid-phase current, a solid-phase potential, an liquid-phase potential, a differential pressure, an internal resistance, a temperature rise rate, and the like.

The chemical parameters of the solid-phase lithium battery include a solid-phase lithium ion concentration, an liquid-phase lithium ion concentration, a particle size of active substances (for example, positive active substances of the lithium battery include $LiNixCoyMn1-x-yO_2$ and lithium cobaltate), a solid-liquid potential, an lithium ion diffusion rate, a solid electrolyte interface (SEI) film thickness (in the first charging and discharging process of an liquid-phase lithium battery, an electrode material and electrolyte react on a solid-liquid phase interface to form a passivation layer covering the surface of the electrode material, the passivation layer is called a SEI film), an lithium dendrite length, and the like.

The physical and chemical quantities comprise at least one state quantity, and the physical parameters and the chemical parameters comprise different working condition data of the lithium battery, so that the physicochemical state quantity distribution function of the solid-phase lithium battery according to embodiments of the invention is substantially corresponding to respective equation expressions of the different working condition data. For example, the solid phase voltage of the solid phase lithium battery varies spatially continuously, so that the solid phase voltage of the solid phase lithium battery corresponds to its own voltage state function. Similarly, the SEI film thickness of the solid-phase lithium battery varies spatially continuously, so that the SEI film thickness of the solid-phase lithium battery corresponds to its own SEI film thickness state function.

The solid-phase physicochemical state quantity and the physicochemical state quantity distribution series function describe an object, but they are not an object themselves, that is, the solid-phase physicochemical state quantity is the time domain expression of the object, and the physicochemical state quantity distribution series function is the frequency domain expression of the object. The language of the time domain is generally used to describe the physicochemical quantity, that is, the physicochemical quantity changes with time. The invention translates the physicochemical quantity into the language of the frequency domain to process, that is, the physicochemical quantity changes with the change of frequency, and then uses the governing equation of the complex frequency domain to observe how the physicochemical quantity changes with the frequency, so that the change of the physical chemical quantities along with time in the time domain can be observed. The invention performs frequency domain conversion calculations, and since the influence of time is included in the physical and chemical quantities in the frequency domain, the differential equation changes from a partial differential equation considering time and space to an ordinary differential equation that only needs to consider space.

The equation expressions of different physicochemical state quantity distribution functions can be established according to experiments or empirical settings, and the specific formula form of the equation expressions is not limited by the disclosure. The method comprises the steps of obtaining initial physical and chemical quantities of the solid-phase lithium battery, establishing a physicochemical state quantity distribution function of the solid-phase lithium battery, and calculating the initial physical and chemical quantities and the physicochemical state quantity distribution function through the Fourier transform algorithm to obtain a corresponding solid-phase ordinary differential equation set in the complex frequency domain.

At step S200, performing a Laplace transform on a partial differential governing equation set of the solid-phase physicochemical state quantity to obtain a solid-phase ordinary differential equation set in a complex frequency domain and obtain an analytical solution in the time domain through an inverse Laplace transform.

Specifically, the analytical solution is a solution obtained by a strict formula. The analytical solution includes the form of a solution of fundamental functions such as fractions, trigonometric functions, exponentials, logarithms, and even infinite series. Given the specific functional form of the solution, any corresponding value can be calculated from the expression of the solution, and the analytical solution is a closed-form function, so any independent variable can be substituted into the analytical function to obtain the correct dependent variable. Therefore, the analytical solution is also called the closed-form solution. The analytical solution is essentially the analytical formula/expression of the function equation (such as the root equation), is the exact solution of the function equation, and can satisfy the function equation at any accuracy.

The initial design of the invention aims at the simulation of the solid-state lithium battery, and the analytical solution calculated by the Laplace transform contains the parameters of the physical and chemical quantities.

At step S300, calculating, according to the analytical solution, a predicted value of the working conditions of the solid-phase lithium battery at any location and at any time in the future.

Specifically, the electrochemical model can not only accurately simulate the external characteristics of the battery, but also simulate the changes in the internal characteristics of the battery (such as the lithium ion concentrations in the electrode and electrolyte, and the other internal physical quantities of the battery that are difficult to measure actually, such as reaction overpotential, and the like). The electrochemical model can deeply describe the microscopic reactions inside the battery.

The model simulation of lithium batteries mainly includes: a lumped particle model (LPM), a single particle model (SPM), a pseudo two-dimension model (P2D), a thermal coupling model, a force coupling model, a force-thermal coupling model, a multi-dimensional edge effect model, a macroscopic temperature model, and the like. The electrochemical models that only involve single-phase or single physical field or weak coupling of physical fields, such as the LPM, the SPM, and the macroscopic temperature model, are called simple electrochemical models. In the simulation of the electrochemical model, the digital twin model of the lithium battery can bring changes in the physical and chemical quantities of the lithium battery such as the voltage, the temperature, and the SEI film thickness under the drive of current.

According to the invention, the Fourier transform and Laplace transform are used to calculate the analytical solution of the distribution functions of the relevant physicochemical state quantity in the electrochemical model, and then calculate the predicted value of the working condition of the solid-phase lithium battery at any time in the future and at any location according to the analytical solution. The predicted value of the working conditions realizes the prediction of the future working condition of the lithium battery. Since the Fourier transform and the Laplace transform are used to predict the future working condition of the lithium battery, it can not only reduce the computational cost, but also improve the future working condition of the lithium battery. The accuracy of the prediction of the situation can be improved, and the cumulative error caused by the actual applications can be reduced.

In another embodiments, said performing the Fourier transform on the physicochemical state quantity distribution function of the solid-phase lithium battery includes the following steps.

At step S110, performing a cosine Fourier transform on the physicochemical state quantity distribution function of the solid-phase lithium battery before relaxation; and calculating the physicochemical state quantity distribution series function in the frequency domain.

Specifically, relaxation is a term of physics, and refers to a process of gradually returning from a certain state to an equilibrium state in a certain gradual physical process. Various relaxation phenomena (e.g., electron relaxation, interfacial reaction relaxation, liquid phase diffusion relaxation, solid phase diffusion relaxation, macroscopic thermal conduction relaxation, etc.) widely exist in the physicochemical processes of the battery because the existence of these relaxation phenomena causes the battery performance to deviate or delay from the description of an idealized model or formula.

The physicochemical state quantity distribution function before relaxation includes the SPM, the solid phase particle concentration distribution in the LPM model, the temperature distribution, etc. According to the invention, the cosine Fourier transform is selected for calculating the physicochemical quantity of the solid-phase lithium battery before relaxation, and the cosine Fourier series after the transform is taken as the initial physical and chemical quantities. The cosine Fourier transform is adopted because any cosine functions are expanded in a space domain, as long as the length of the space domain is integral multiple of the cosine frequency, the first derivatives of the cosine function at both end points of the space domain are which is similar to a shutdown state, physical quantity is not exchanged with the outside after shutdown, a state field is 0 in a first differential at a space boundary. At the moment, the physical quantity inside the field is not uniform, only the field relaxation in the space domain is performed, and the physical quantity exchange with an outside system is not performed.

The partial differential governing equation set of the solid-phase physical chemical quantity comprises a governing equation, a boundary condition and an initial condition. The governing equation is a mathematical expression that characterizes an electrochemical model of the solid-phase lithium battery for a spatial distribution of the physical and chemical quantities as a function of time. The boundary condition is an exchange condition of a solid phase and the outside. The initial condition is an initial value of the physicochemical state quantity distribution function.

At step S210, performing a frequency domain conversion on the governing equation and the boundary condition based on the Laplace transform to obtain a complex frequency domain governing equation and a complex frequency domain boundary condition, so as to obtain a solid-phase ordinary differential equation set in the complex frequency domain, wherein the complex frequency domain solid-phase ordinary differential equation set comprises the complex frequency domain governing equation, the complex frequency domain boundary condition and the physicochemical state quantity distribution series function in the frequency domain.

At step S220, solving the complex frequency domain solid-phase ordinary differential equation set, and calculating the solved result using the inverse Laplace transform to obtain the analytical solution of infinite series in the time domain.

Specifically, most of the governing equations in the electrochemical model are parabolic partial differential equations in the form of $$\frac{\partial T}{\partial t} = a\frac{\partial^2 T}{\partial \chi^2}.$$

In fact, the mathematical description in the electrochemical model is generally the partial differential equation (PDE), the boundary condition (BC), and the initial condition (IC). The boundary condition refers to the change law of the variables or their derivatives that are solved on the boundary of the solution area with time and space. The boundary condition is the premise that the governing equation has a definite solution. For any problem, the boundary condition needs to be given. In one embodiment, the boundary condition of the invention is the exchange between the solid phase and the outside, such as the exchange of carriers, the exchange of heat or the exchange of energy.

After establishing the distribution function of the physicochemical state quantity of the solid-phase lithium battery before relaxation, the cosine Fourier algorithm is used to calculate the distribution function of the physicochemical state quantity before relaxation to obtain the corresponding complex frequency domain solid-phase ordinary differential equation set. Continuing with the above example, the complex frequency domain solid-phase ordinary differential equation set corresponding to the solid-phase voltage can be calculated and obtained, and the complex frequency-domain solid-phase ordinary differential equation set corresponding to the SEI film thickness can also be calculated and obtained.

According to the definition of the Laplace transform algorithm, the governing equation, the boundary condition and the initial condition in the complex frequency domain solid-phase ordinary differential equation set are subjected to frequency domain conversion, and the complex frequency domain solid-phase ordinary differential equation set in the frequency domain can be obtained through calculation and comprises the governing equation, the boundary condition and the initial condition in the frequency domain. Then, a complex frequency domain solid phase ordinary differential equation set in the frequency domain composed of the governing equation, the boundary condition and the initial condition is solved, an analytical solution of the complex frequency domain solid phase ordinary differential equation set in the time domain is obtained by utilizing table look-up or inverse Laplace transform, and the analytical solution is used for representing the physicochemical parameters (namely the physical and chemical quantities of the invention) of the electrochemical model in the time domain.

At step S310, substituting spatial coordinates and future time of a state quantity to be solved into the corresponding analytical solution to calculate the predicted values of the working conditions of the solid-phase lithium battery at the future time and the location corresponding to the spatial coordinates.

Specifically, the physical and chemical quantities at different times and different locations can be calculated by substituting the spatial coordinates and the future time, which are the state quantities required for the solid-phase lithium battery and are intended to predict the physical and chemical quantities, into the respective analytical solutions. The obtained physical and chemical quantities are then used as the internal output of the model and put into the electrochemical model for decoupling. In simple electrochemical models, there are often only one or more governing partial differential equations that are not related or weakly coupled to each other. Due to the weak or no coupling among the governing partial differential equations in the simplified electrochemical model (such as LPM, SPM, macroscopic temperature model and the like), the real-time physical and chemical quantities of the entire electrochemical model can be obtained without decoupling.

Exemplarily, lithium dendrites are dendritic metallic lithium formed when lithium ions are reduced during charging of the lithium battery. The growth of lithium dendrites leads to the instability of the electrode and electrolyte interface during the cycle of lithium battery and destroy of the formed SEI film. The lithium dendrites can continuously consume the electrolytes during the growth process and cause irreversible delocation of lithium, so that dead lithium is formed to cause low Coulombic efficiency. The formation of lithium dendrites can even pierce the diaphragm and cause internally a short circuit of the lithium battery, thereby causing thermal runaway of the battery to cause combustion and explosion. Then, assuming that the required state quantity is the length of the lithium dendrite, and the spatial coordinates P(xm, ym, zm) of the target portion m of the lithium battery that the time (i.e., the future time Tm) to be predicted, which are desired by the user, are substituted into the analytical solution of the complex frequency-domain solid-phase ordinary differential equation set corresponding to the thickness of the SEI film, the lithium dendrite length L of the solid-phase lithium battery at the future time Tm and the target portion m can be calculated.

At step S400, comparing the predicted value of the working conditions with the corresponding threshold value.

At step S500, generating prompt information for notification and early warning, when the predicted value of the working conditions exceeds the corresponding threshold value.

Specifically, each state quantity in the physical and chemical quantities has a preset threshold value for ensuring safe, healthy and efficient operation of the lithium battery. After judging whether each state quantity in the physical and chemical quantities exceeds the corresponding threshold value, the invention carries out early warning of different levels according to the judgment result. Meanwhile, if the solid-phase physical and chemical quantities in the battery at a certain moment continues to operate under certain practical working conditions, the safety accident is possibly caused, and at the moment, simulation prediction is carried out according to the current solid-phase physical and chemical quantities, the working condition which can be adopted by the battery within a certain period of time after the moment and cannot cause the safety accident is obtained, and the working condition limit of the battery in the future is reported. The space coordinates and the future time of the state quantity is substituted into the corresponding analytical solution to solve and predict the future working condition of the lithium battery.

For example, the predicted value of the operating conditions comprises the temperature T and the lithium dendrite length L of the solid-phase lithium battery. If the temperature T of the solid-phase lithium battery exceeds a preset temperature threshold value, but the length L of the lithium dendrite of the solid-phase lithium battery does not exceed the preset length threshold value, only prompt information is generated to notify, early warn and inform that the temperature exceeds the standard. Of course, if the temperature T of the solid-phase lithium battery exceeds the preset temperature threshold and the length L of the lithium dendrite of the solid-phase lithium battery exceeds the preset length threshold, only prompt information is generated to notify early warning to inform that the temperature exceeds the standard and the length of the lithium dendrite exceeds the standard.

Preferably, the thresholds corresponding to different state quantities can be set according to requirements. According to embodiments of the invention three thresholds are established as follows: an economic threshold, a reliability threshold, a safety threshold. The economic threshold is established based on the economic cost of charging and discharging, the reliability threshold is determined based on the voltage change of the electrode caused by the change of the solid-phase lithium ions along with the time under the self-discharging condition and the voltage threshold of the side reaction, and the safety threshold is determined based

| on the speed of the lithium ions to diffuse out of the solid phase and the drastic temperature and voltage change caused by the speed. According to the invention, an alarm and early warning for the corresponding self-discharge situation is provided when any two of the three threshold values are exceeded.

According to the method, after the analytical solution of the complex frequency domain solid-phase ordinary differential equation set corresponding to each physicochemical quantity is obtained through calculation based on the Fourier transform and the Laplace transform, the time-space parameters (namely the space coordinates and the future time of the state quantity obtained through the method) are substituted, so that the state quantity of the lithium battery electrochemical model at different times and different locations (namely the working condition predicted value of the method) can be predicted, which is more computationally efficient and more accurate than the existing method. In addition, the predicted values of the working conditions of the lithium battery at different times and different locations are solved and obtained through using the Fourier transform and the Laplace transform which can greatly prompt the accuracy of the working condition prediction of the lithium battery.

The invention prompts and alarms the predicted value of working conditions exceeding the threshold value, and predicts and screens the lithium battery with risk of runaway in advance, which not only saves the cost of the out of control monitoring of the lithium battery, but also improves the safety of battery modules. In addition, the invention is favorable for eliminating the potential safety hazard of the lithium battery out of control in time by carrying out the out of control grading early warning, greatly reducing the probability of the lithium battery out of control, being favorable for guaranteeing the life safety of the public and reducing property loss.

The invention provides an analytical solution to the solid phase simulation of the electrochemical model by using the Fourier transform and the Laplace transform, and can greatly reduce the simulation speed of the simplified electrochemical model in the solid phase. The invention can simply place the solid phase in the electrochemical model into the edge computing chip for simulation, and a single chip can realize parallel computing, thereby realizing high-flux simulation and increasing the simulation speed by tens of thousands of times. The physicochemical quantity changes obtained from the simulation based on the electrochemical model are the description of the physical and chemical processes actually occurring inside the lithium battery, and the prediction of the future situation of the lithium battery is more accurate (especially in extreme cases), so that the future condition of the lithium battery can be predicted accordingly. The working conditions are restricted to prevent the lithium battery from operating under a working condition that may cause danger or emergency. At the same time, can be given to the danger which possibly generates, so that the lithium battery can be operated safely, healthily and efficiently.

In another aspect, the invention also provides a system for predict working conditions of lithium batteries. As shown in FIG. 2, the system includes a first calculation module 10, a second calculation module 20, and a prediction module 30.

The first calculation module 10 is configured to perform a Fourier transform on a physicochemical state quantity distribution function of a solid-phase lithium battery to calculate a physicochemical state quantity distribution series function in a frequency domain and obtain a solid-phase physicochemical state quantity in the frequency domain according to the physicochemical state quantity distribution series function. The physicochemical state quantity distribution function is an equation expression of physical and chemical quantities of the solid-phase lithium battery that change continuously in space in a time domain. The physical and chemical quantities comprise at least one state quantity of physical parameters and chemical parameters of the solid-phase lithium battery.

The second calculation module 20 is configured to perform a Laplace transform on a partial differential governing equation set of the solid-phase physicochemical state quantity to obtain a solid-phase ordinary differential equation set in a complex frequency domain and obtain an analytical solution in the time domain through an inverse Laplace transform.

The prediction module 30 is configured to calculate a predicted value of the working conditions of the solid-phase lithium battery at any location and at any time in the future according to the analytical solution.

In some embodiments, the first computing module 10 includes: a first conversion unit configured to perform a cosine Fourier transform on the physicochemical state quantity distribution function of the solid-phase lithium battery before relaxation; and calculate the physicochemical state quantity distribution series function in the frequency domain.

In some embodiments, the partial differential governing equation set of the solid-phase physical chemical quantity comprises a governing equation, a boundary condition and an initial condition, wherein the governing equation is a mathematical expression that characterizes an electrochemical model of the solid-phase lithium battery for a spatial distribution of the physical and chemical quantities as a function of time, the boundary condition is an exchange condition of a solid phase and the outside, and the initial condition is an initial value of the physicochemical state quantity distribution function.

In some embodiments, the second calculating module 20 comprises a second conversion unit and an inverse Laplace calculation unit.

The second conversion unit is configured to perform a frequency domain conversion on the governing equation and the boundary condition based on the Laplace transform to obtain a complex frequency domain governing equation and a complex frequency domain boundary condition, so as to obtain a solid-phase ordinary differential equation set in the complex frequency domain, wherein the complex frequency domain solid-phase ordinary differential equation set comprises the complex frequency domain governing equation, the complex frequency domain boundary condition and the physicochemical state quantity distribution series function in the frequency domain.

The inverse Laplace calculation unit is configured to solve the complex frequency domain solid-phase ordinary differential equation set, and calculate the solved result using the inverse Laplace transform to obtain the analytical solution of infinite series in the time domain.

In some embodiments, the prediction module 30 includes a prediction unit configured to substitute spatial coordinates and future time of a state quantity to be solved into the corresponding analytical solution to calculate the predicted values of the working conditions of the solid-phase lithium battery at the future time and the location corresponding to the spatial coordinates.

In some embodiments, the system also includes a comparison module, configured to compare the predicted value of the working conditions with a corresponding threshold value; and an alarm module, configured to generate prompt information for notification and early warning, when the predicted value of the working conditions exceeds the corresponding threshold value.

It should be noted that the exemplary embodiment is a system embodiment corresponding to the method embodiment as disclosed above. For specific effects, please refer to the above-mentioned method embodiment, which will not be repeated herein.

Those skilled in the art can clearly understand that for the convenience and brevity of description, only the division of the above-mentioned modules is used as an example for illustration. In practical applications, the above-mentioned functions can be assigned by different modules according to needs. The internal structure of the device is divided into different units or modules to complete all or part of the functions described above. Each module in the embodiments can be integrated in one processing unit, or each unit can exist separately physically, or two or more units can be integrated in one processing unit, and the above-mentioned integrated units can be implemented in the form of hardware, can also be implemented in the form of software program units. In addition, the specific names of the modules are only for the convenience of distinguishing each other, and are not used to limit the protection scope of the invention.

In the above-mentioned embodiments, the descriptions of each embodiment have their own emphases, and for parts that are not described or recorded in detail in a certain embodiment, reference may be made to relevant descriptions of other embodiments.

Those skilled in the art can appreciate that the units and steps of the examples described in conjunction with the embodiments disclosed herein can be implemented by electronic hardware, or a combination of computer software and electronic hardware. Whether these functions are implemented by hardware or software depends on the specific application and design constraints of the technical solution. Skilled artisans may use different methods to implement the described functions for each specific application, but such implementation should not be regarded as exceeding the scope of the invention.

In the embodiments provided in this disclosure, it should be understood that the disclosed system and method may be implemented in other ways. For example, the system embodiments described above are only illustrative. For example, the division of the modules or units is only a logical function division. There may be other division methods in actual implementation, for example, multiple units or components may be combined or integrated into another system, or some features may be omitted, or not implemented. In another embodiments, the mutual coupling or direct coupling or communication connection shown or discussed may be through some interfaces, and the indirect coupling or communication connection of devices or units may be in electrical, mechanical or other forms.

The modules and units described as separate components may or may not be physically separated, and the components shown as units may or may not be physical units, that is, they may be located in one place, or may be distributed to multiple network units. Part or all of the units can be selected according to actual needs to achieve the purpose of the solution of this embodiment.

In addition, each functional unit in each embodiment of the invention may be integrated into one processing unit, each unit may exist separately physically, or two or more units may be integrated into one unit. The above-mentioned integrated units can be implemented in the form of hardware or in the form of software functional units.

It should be understood that although the various steps in the flow chart of the accompanying drawings are displayed in sequence according to the arrows, these steps are not necessarily executed in sequence in the order indicated by the arrows. Unless otherwise specified herein, there is no strict order restriction on the execution of these steps, and they can be executed in other orders. Moreover, at least some of the steps in the flowcharts of the accompanying drawings may include multiple sub-steps or multiple stages, and these sub-steps or stages may not necessarily be executed at the same time, but may be executed at different times, and the order of execution is also It is not necessarily performed sequentially, but may be performed alternately or alternately with at least a part of other steps or sub-steps or stages of other steps.

It should be noted that the above embodiments can be freely combined as required. The above is only a preferred embodiment of the invention, it should be pointed out that, for those of ordinary skill in the art, without departing from the principle of the invention, some improvements and modifications can also be made, and these improvements and modifications can also be made. It should be regarded as the protection scope of the invention.

The foregoing description of the exemplary embodiments of the invention has been presented only for the purposes of illustration and description and is not intended to be exhaustive or to limit the invention to the precise forms disclosed. Many modifications and variations are possible in light of the above teaching. The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the invention pertains without departing from its spirit and scope. Accordingly, the scope of the invention is defined by the appended claims rather than the foregoing description and the exemplary embodiments described therein.

What is claimed is:

1. A method for predicting working conditions of lithium batteries, comprising:

performing a Fourier transform on a physicochemical state quantity distribution function of a solid-phase lithium battery to calculate a physicochemical state quantity distribution series function in a frequency domain and obtain a solid-phase physicochemical state quantity in the frequency domain according to the physicochemical state quantity distribution series function, wherein the physicochemical state quantity distribution function is an equation expression of physical and chemical quantities of the solid-phase lithium battery that change continuously in space in a time domain, and wherein the physical and chemical quantities comprise at least one state quantity of physical parameters and chemical parameters of the solid-phase lithium battery;

performing a Laplace transform on a partial differential governing equation set of the solid-phase physicochemical state quantity to obtain a solid-phase ordinary differential equation set in a complex frequency domain and obtain an analytical solution in the time domain through an inverse Laplace transform; and calculating, according to the analytical solution, a predicted value of the working conditions of the solid-phase lithium battery at any location and at any time in the future.

2. The method of claim 1, wherein said performing the Fourier transform on the physicochemical state quantity distribution function of the solid-phase lithium battery comprises:

performing a cosine Fourier transform on the physicochemical state quantity distribution function of the solid-phase lithium battery before relaxation; and calculating the physicochemical state quantity distribution series function in the frequency domain.

3. The method of claim 1, wherein the partial differential governing equation set of the solid-phase physical chemical quantity comprises a governing equation, a boundary condition and an initial condition, wherein the governing equation is a mathematical expression that characterizes an electrochemical model of the solid-phase lithium battery for a spatial distribution of the physical and chemical quantities as a function of time, the boundary condition is an exchange condition of a solid phase and the outside, and the initial condition is an initial value of the physicochemical state quantity distribution function; and wherein said performing the Laplace transform on the partial differential governing equation set of the solid-phase physicochemical state quantity comprises:

performing a frequency domain conversion on the governing equation and the boundary condition based on the Laplace transform to obtain a complex frequency domain governing equation and a complex frequency domain boundary condition, so as to obtain a solid-phase ordinary differential equation set in the complex frequency domain, wherein the complex frequency domain solid-phase ordinary differential equation set comprises the complex frequency domain governing equation, the complex frequency domain boundary condition and the physicochemical state quantity distribution series function in the frequency domain; and solving the complex frequency domain solid-phase ordinary differential equation set, and calculating the solved result using the inverse Laplace transform to obtain the analytical solution of infinite series in the time domain.

4. The method of claim 1, wherein said calculating the predicted value of the working conditions of the solid-phase lithium battery comprises:

substituting spatial coordinates and future time of a state quantity to be solved into the corresponding analytical solution to calculate the predicted values of the working conditions of the solid-phase lithium battery at the future time and the location corresponding to the spatial coordinates.

5. The method of claim 1, wherein said calculating the predicted value of the working conditions of the solid-phase lithium battery comprises:

comparing the predicted value of the working conditions with a corresponding threshold value; and generating prompt information for notification and early warning, when the predicted value of the working conditions exceeds the corresponding threshold value.

6. A system for predicting working conditions of lithium batteries, comprising:

a first calculation module, configured to perform a Fourier transform on a physicochemical state quantity distribution function of a solid-phase lithium battery to calculate a physicochemical state quantity distribution series function in a frequency domain and obtain a solid-phase physicochemical state quantity in the frequency domain according to the physicochemical state quantity distribution series function, wherein the physicochemical state quantity distribution function is an equation expression of physical and chemical quantities of the solid-phase lithium battery that change continuously in space in a time domain, and wherein the physical and chemical quantities comprise at least one state quantity of physical parameters and chemical parameters of the solid-phase lithium battery;

a second calculation module, configured to perform a Laplace transform on a partial differential governing equation set of the solid-phase physicochemical state quantity to obtain a solid-phase ordinary differential equation set in a complex frequency domain and obtain an analytical solution in the time domain through an inverse Laplace transform; and a prediction module, configured to calculate a predicted value of the working conditions of the solid-phase lithium battery at any location and at any time in the future according to the analytical solution.

7. The system of claim 6, wherein the first calculating module comprises a first conversion unit, configured to:

perform a cosine Fourier transform on the physicochemical state quantity distribution function of the solid-phase lithium battery before relaxation; and calculate the physicochemical state quantity distribution series function in the frequency domain.

8. The system of claim 6, wherein the partial differential governing equation set of the solid-phase physical chemical quantity comprises a governing equation, a boundary condition and an initial condition, wherein the governing equation is a mathematical expression that characterizes an electrochemical model of the solid-phase lithium battery for a spatial distribution of the physical and chemical quantities as a function of time, the boundary condition is an exchange condition of a solid phase and the outside, and the initial condition is an initial value of the physicochemical state quantity distribution function; and wherein the second calculation module comprises a second conversion unit, configured to perform a frequency domain conversion on the governing equation and the boundary condition based on the Laplace transform to obtain a complex frequency domain governing equation and a complex frequency domain boundary condition, so as to obtain a solid-phase ordinary differential equation set in the complex frequency domain, wherein the complex frequency domain solid-phase ordinary differential equation set comprises the complex frequency domain governing equation, the complex frequency domain boundary condition and the physicochemical state quantity distribution series function in the frequency domain; and an inverse Laplace calculation unit, configured to solve the complex frequency domain solid-phase ordinary differential equation set, and calculate the solved result using the inverse Laplace transform to obtain the analytical solution of infinite series in the time domain.

9. The system of claim 6, wherein the prediction module comprises:

a prediction unit, configured to substitute spatial coordinates and future time of a state quantity to be solved into the corresponding analytical solution to calculate the predicted values of the working conditions of the solid-phase lithium battery at the future time and the location corresponding to the spatial coordinates.

10. The system of claim 6, further comprising:

a comparison module, configured to compare the predicted value of the working conditions with a corresponding threshold value; and an alarm module, configured to generate prompt information for notification and early warning, when the predicted value of the working conditions exceeds the corresponding threshold value.

* * * * *